US012788787B2

(12) United States Patent
Lee et al.

(10) Patent No.: US 12,788,787 B2
(45) Date of Patent: Nov. 10, 2026

(54) LACTIC ACID BACTERIUM FOR TREATMENT OF AROMATIC L-AMINO ACID DECARBOXYLASE DEFICIENCY

(71) Applicants: Wang-Tso Lee, Taipei City (CN); Su Ching Hu, Taipei City (CN)

(72) Inventors: Wang-Tso Lee, Taipei City (CN); Su Ching Hu, Taipei City (CN); Lee Chin Wong, Taipei City (CN)

(73) Assignees: Wang-Tso Lee, Taipei City (TW); Su Ching Hu, Taipei City (TW)

( * ) Notice: Subject to any disclaimer, the term of this patent is extended or adjusted under 35 U.S.C. 154(b) by 479 days.

(21) Appl. No.: 18/033,232

(22) PCT Filed: Oct. 22, 2021

(86) PCT No.: PCT/CN2021/125800

§ 371 (c)(1),
(2) Date: Apr. 21, 2023

(87) PCT Pub. No.: WO2022/083754

PCT Pub. Date: Apr. 28, 2022

(65) Prior Publication Data

US 2023/0390347 A1 Dec. 7, 2023

Related U.S. Application Data

(60) Provisional application No. 63/094,925, filed on Oct. 22, 2020.

(51) Int. Cl.
*A61K 35/747* (2015.01)
*A61P 25/28* (2006.01)

(52) U.S. Cl.
CPC ............ *A61K 35/747* (2013.01); *A61P 25/28* (2018.01)

(58) Field of Classification Search
CPC .............................. A61K 35/747; A61P 25/28
See application file for complete search history.

(56) References Cited

FOREIGN PATENT DOCUMENTS

| | | | |
|---|---|---|---|
| CN | 105002109 | A | 10/2015 |
| WO | 2018/014225 | A1 | 1/2018 |
| WO | 2020/156417 | A1 | 8/2020 |
| WO | 2020/156418 | A1 | 8/2020 |

OTHER PUBLICATIONS

Jian-Fu Liao, et al., "Lactobacillus plantarum PS128 alleviates neurodegenerative progression in 1-methyl-4-phenyl-1,2,3,6-tetrahydropyridine-induced mouse models of Parkinson's disease", Elsevier, Brian, Behavior, and Immunity, Jul. 30, 2020, pp. 26-46, vol. 90.

Jian-Fu Liao, et al., "Lactobacillus plantarum PS128 ameliorates 2,5-Dimethoxy-4- iodoamphetamine-induced tic-like behaviors via its influences on the microbiota-gut-brain-axis", Elsevier, Brian Research Bulletin Jul. 25, 2019, pp. 59-73, vol. 153.

X.R. Chen, et al., "Aromatic L-amino acid decarboxylase deficiency: a report of two cases and literature review", J. Clin. Pediatr, May 31, 2019, pp. 365-368, vol. 37.

Y.L. Xia, et al., "Research Progress on improving exercise stress by supplementing probiotics and its mechanism", Chin. J. Sports Med, Aug. 31, 2019, pp. 704-711, vol. 38, No. 8.

International Search Report for PCT/CN2021/125800 dated Jan. 19, 2022.

Written Opinion Report for PCT/CN2021/125800 dated Jan. 19, 2022.

*Primary Examiner* — Robert A Zeman
(74) *Attorney, Agent, or Firm* — Sughrue Mion, PLLC

(57) ABSTRACT

Provided is a method of treating aromatic L-amino acid decarboxylase (AADC) deficiency in a subject in need thereof, including administering to the subject an effective amount of *Lactobacillus plantarum* subsp. *plantarum* PS128.

13 Claims, 6 Drawing Sheets

LACTIC ACID BACTERIUM FOR TREATMENT OF AROMATIC L-AMINO ACID DECARBOXYLASE DEFICIENCY

CROSS REFERENCE TO RELATED APPLICATIONS

This application is a National Stage of International Application No. PCT/CN2021/125800 filed Oct. 22, 2021, claiming priority based on U.S. Provisional Patent Application No. 63/094,925 filed Oct. 22, 2020.

BACKGROUND

1. Technical Field

This disclosure relates to a lactic acid bacterium, and more particularly relates to the PS128 strain of lactic acid bacterium for treatment of aromatic L-amino acid decarboxylase deficiency in a subject in need thereof.

2. Description of Related Art

Aromatic L-amino acid decarboxylase (AADC) deficiency is a disease resulted from the malfunction or loss of function of an enzyme responsible for the production of neurotransmitters. Specifically, AADC deficiency is caused by mutations in the dopa decarboxylase (DDC) gene. When the neurotransmitters are not being produced properly, the nervous system is not able to carry out its normal functions. Accordingly, individuals affected by this disease can have problems in coordinating movements, hypotonia, and muscle stiffness, and consequently, difficulty to move.

As a genetic disease, affected individuals usually show symptoms during the first year of life, and there is severe delay in reaching development milestones such as walking and talking. AADC deficiency may also affect the autonomic nervous system, and thus the symptoms extend to involuntary body processes such as control of blood pressure, heart rate, and body temperature. Other autonomic symptoms may include droopy eye lids (known as ptosis or blepharoptosis), constriction of the pupils of eyes (known as miosis or myosis), inappropriate or impaired sweating, nasal congestion, drooling, gastroesophageal reflux, low blood sugar (also known as hypoglycemia), fainting (or syncope), and cardiac arrest.

There is currently no cure for AADC deficiency. Presently, different medications are used to help treat the signs and symptoms of the disease. However, although certain combinations of medications may help some people, there is no proven strategy that relieves the symptoms of all individuals with this disease. The efficacy of a particular treatment in an individual depends on the exact change in the DDC gene which in turn determines the extent of the AADC enzyme function, causing a wide variation in the severity of symptoms in individuals with the disease.

Since the neurological symptoms in a child with AADC deficiency is resulted from the lack of certain neurotransmitters, one line of the treatments aims to supplement neurotransmitters to increase their availability in the body. For example, dopamine receptor agonists, monoamine oxidase (MAO) inhibitor and pyridoxine (vitamin B6) are given to patients. Other treatments may depend on the symptoms of each individual, including anticholinergic agents to treat movement disorders, seizure medication, gastrointestinal medications and melatonin to treat sleep disturbances. Therefore, there remains an unmet need to improve general neurological functions for AADC deficiency patients and alleviating symptoms of AADC deficiency.

SUMMARY

The present disclosure provides a method for treating aromatic L-amino acid decarboxylase (AADC) deficiency in a subject in need thereof that comprises a step of administering an effective amount of *Lactobacillus plantarum* subsp. *plantarum* PS128 to the subject. The isolated lactic acid bacterium used in the present disclosure is *Lactobacillus plantarum* subsp. *plantarum* PS128 and deposited under DSMZ Accession No. DSM 28632. In one embodiment, the effective amount of PS128 is at least $1\times10^9$ CFU, at least $1\times10^{10}$ CFU or at least $1\times10^{11}$ CFU, including $1\times10^9$ CFU, $2\times10^9$ CFU, $3\times10^9$ CFU, $4\times10^9$ CFU, $5\times10^9$ CFU, $6\times10^9$ CFU, $7\times10^9$ CFU, $8\times10^9$ CFU, $9\times10^9$ CFU, $1\times10^{10}$ CFU, $2\times10^{10}$ CFU, $3\times10^{10}$ CFU, $4\times10^{10}$ CFU, $5\times10^{10}$ CFU, $6\times10^{10}$ CFU, $7\times10^{10}$ CFU, $8\times10^{10}$ CFU, $9\times10^{10}$ CFU, $1\times10^{11}$ CFU, $2\times10^{11}$ CFU, $3\times10^{11}$ CFU, $4\times10^{11}$ CFU, $5\times10^{11}$ CFU, $6\times10^{11}$ CFU, $7\times10^{11}$ CFU, $8\times10^{11}$ CFU, and $9\times10^{11}$ CFU, but not limited thereto. In at least one embodiment, the composition is administered to the subject at least once a day.

In one embodiment of the present disclosure, the composition is administered to the subject for at least 1 week, at least 2 weeks, at least 3 weeks, at least 4 weeks, at least 5 weeks or at least 6 weeks. In another embodiment, the composition is administered to the subject for at least 1 month, at least 2 months, at least 3 months, at least 4 months, at least 5 months or at least 6 months. In another embodiment, the composition is administered to the subject for at least 1 year, at least 2 years or at least 3 years.

In at least one embodiment of the present disclosure, a composition that comprises *Lactobacillus plantarum* subsp. *plantarum* PS128 and a carrier thereof is provided. In one embodiment of the present disclosure, the composition is a pharmaceutical composition further comprising a pharmaceutically acceptable carrier thereof. In another embodiment of the present disclosure, the pharmaceutically acceptable carrier may be a physiologically acceptable excipient or diluent. In yet another embodiment of the present disclosure, the examples of the physiologically acceptable excipient or diluent include, but are not limited to, lactose, starch, dextrin, cyclodextrin, sodium carboxymethyl starch, carboxylated starch propionate, microcrystalline cellulose, carboxymethyl cellulose, maltodextrin and magnesium stearate.

In at least one embodiment, the composition is orally administered to the subject. In one embodiment of the present disclosure, the composition comprising the *Lactobacillus plantarum* subsp. *plantarum* PS128 as a sole active ingredient for preventing or treating the ADCC deficiency in a subject in need thereof.

In at least one embodiment of the present disclosure, after the administration of *Lactobacillus plantarum* subsp. *plantarum* PS128, at least one of motor activity and basal locomotor activity is increased. In at least one embodiment, after the administration of *Lactobacillus plantarum* subsp. *plantarum* PS128, at least one of endurance, balance, coordination, physical condition and motor planning is improved. In at least one embodiment, after the administration of *Lactobacillus plantarum* subsp. *plantarum* PS128, a neurotransmitter level is significantly increased in the subject. For example, the neurotransmitter is selected from the group consisting of dopamine (DA), serotonin (5-HT) and 5-hydroxyindoleacetic acid (5-HIAA). In at least one embodiment, a neurotransmitter level is significantly decreased in the subject. For example, the level of L-3,4-dihydroxyphenylalanine (L-DOPA) is significantly decreased in a subject being administered with PS128. In at least one embodiment, the administration increases the dopaminergic and serotoninergic function in the subject.

In at least one embodiment of the present disclosure, the administration of *Lactobacillus plantarum* subsp. *plantarum* PS128 improves neuron branching in the subject. In at least one embodiment, the administration improves neuron function and connectivity.

In at least one embodiment of the present disclosure, the administration of *Lactobacillus plantarum* subsp. *plantarum* PS128 comprises improvement of at least one symptom of L-amino acid decarboxylase (AADC) deficiency in the subject. In at least one embodiment, the symptom includes sweating, dystonia, irritability and sleep disturbance. In at least one embodiment, the symptom is a neurological symptom, including motor activity, basal locomotor activity, balance, coordination, physical condition, motor planning, and any combination thereof.

BRIEF DESCRIPTION OF THE DRAWINGS

The present disclosure can be more understood by reading the following descriptions of the embodiments, with reference made to one or more of the accompanying drawings below.

FIG. 4A shows the result of Sholl analysis on the lengths of neuron processes in mice treated with PS128 or PBS. #: ko-pbs vs. ko-probiotics, $p<0.05$; *: ko-pbs vs. wt-pbs, $p<0.05$. Statistical analysis was carried out by t-test and Mann-Whitney U test. FIG. 4B shows the images of neuronal branching of neurons in DDC gene knockout mutant mice treated with or without PS128. ko-probiotics: mutant mice with the DDC gene knockout treated with PS128; ko-pbs: mutant mice with the DDC gene knockout treated with phosphate buffered saline; wt-pbs: wildtype mice treated with phosphate buffered saline.

DETAILED DESCRIPTION OF THE EMBODIMENTS

Figure 1:
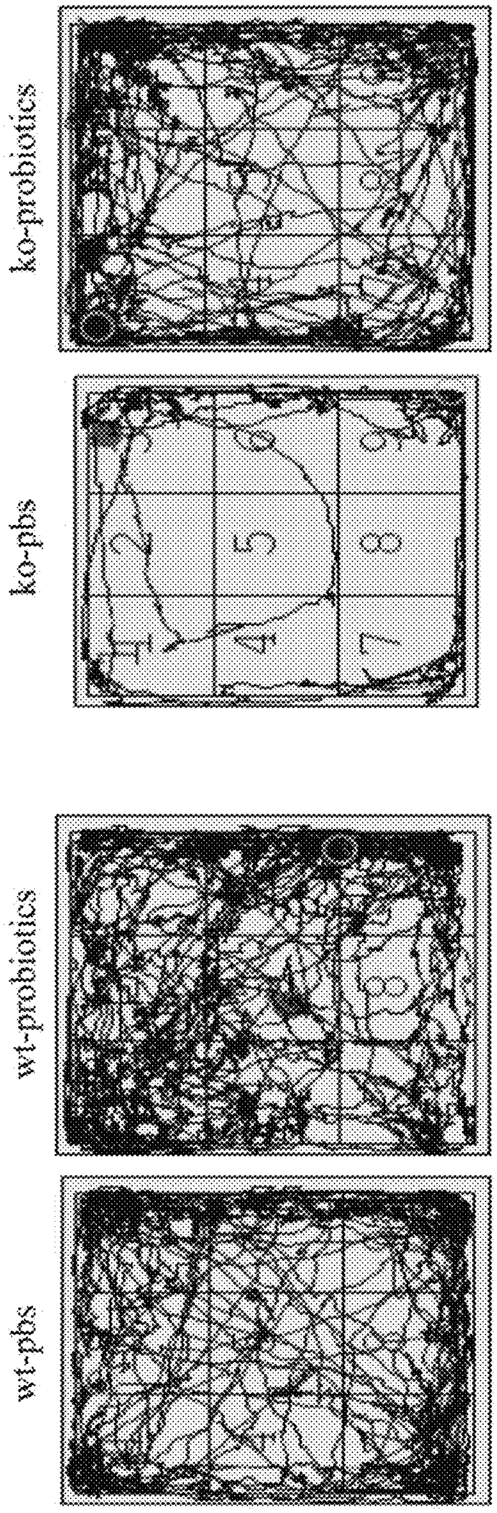
FIG. 1 shows the tracking of mice activity in open field before and after PS128 treatment. wt-pbs: wildtype mice treated with phosphate buffered saline; wt-probiotics: wildtype mice treated with PS128; ko-pbs: mutant mice with the DDC gene knockout treated with phosphate buffered saline; ko-probiotics: mutant mice with the DDC gene knockout treated with PS128.

The following examples are used for illustrating the present disclosure. A person skilled in the art can easily conceive the other advantages and effects of the present disclosure. The present disclosure can also be implemented by different cases enacted. The details of the descriptions can also be based on different perspectives and applications in various modifications and changes that do not depart from the scope of this disclosure.

All terms including descriptive or technical terms which are used herein should be construed as having meanings that are obvious to one of ordinary skill in the art. However, the terms may have different meanings according to an intention of one of ordinary skill in the art, case precedents, or the appearance of new technologies. Also, some terms may be arbitrarily selected by the applicant, and in this case, the meaning of the selected terms will be described in detail in the descriptions of the present disclosure. Thus, the terms used herein have to be defined based on the meaning of the terms together with the descriptions throughout the specification.

Also, when a part "includes" or "comprises" a component or a step, unless there is a particular description contrary thereto, the part can further include other components or other steps, not excluding the others.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The phrase "an effective amount" refers to the amount of an active ingredient that is required to result in a reduction, inhibition or prevention of the behavioral disorder, abnormality or symptom in the individual. An effective amount will vary, as recognized by those skilled in the art, depending on routes of administration, excipient usage, and the possibility of co-usage with other therapeutic treatment.

The term "individual" as used herein may be interchangeable with "subject" or "patient" and includes a single biological organism, of which a neurodevelopmental disorder may occur including, but not limited to, animals and in particular vertebrates such as mammals, e.g., human beings.

The term "individual in need of the treatment" refers to a person expressing or suffering from one or more symptoms related to AADC deficiency. An appropriately qualified person is able to identify such an individual in need of treatment using standard protocols or guidelines.

The term "condition" or "symptom" as used herein refers to symptoms expressed by a subject diagnosed of AADC deficiency.

The term "treating" or "treatment" in AADC deficiency as used herein refers to amelioration, reduction or improvement in the severity or frequency, to whatever extent, of one or more of the symptoms of AADC deficiency.

The term "improvement" as used herein refers to prevention or reduction in the severity or frequency, to whatever extent, of one or more of the symptoms or abnormalities expressed by the individual diagnosed with AADC deficiency. The improvement is either observed by the individual taking the treatment themselves or by another person.

Many examples have been used to illustrate the present disclosure. The examples cited below should not be taken as a limit to the scope of the disclosure.

EXAMPLES

*Lactobacillus plantarum* subsp. *plantarum* PS128 has been deposited under Budapest Treaty at Leibniz Institute DSMZ-German Collection of Microorganisms and Cell Cultures (Inhoffenstr. 7 B, D-38124 Braunschweig, Germany)

on Mar. 31, 2014 and has been given the DSMZ Accession No. DSM 28632 by the International Depositary Authority. This biological material was subjected to the viability test and passed.

Example 1. Administration of PS128 Improves Motor Activity

To examine the effects of PS128 on the general motor function in an animal, open field test (OFT) and rotarod test were adopted. Specifically, before the tests, phosphate buffered saline (PBS) and probiotics PS128 (provided by Bened Biomedical Co., Ltd.) at the dose of $10^9$ CFU/mouse/day were orally administered to the wildtype C57BL/6JNarl mice and the mutant B6 Nestin-Cre/DDC flox/flox mice for 6 weeks. The mutant B6 Nestin-Cre/DDC flox/flox mice have conditionally knockout the DDC gene and serve as the animal model of AADC deficiency.

The open field test is a common measure of exploratory behavior and general activity in both mice and rats, where both the quality and quantity of the activity can be measured. For the open field test for motor activity, each mouse was monitored for 15 min under observation by a video camera in an open field arena (40×40×50 cm in dimension). The arena was divided into 9 squares on the computer tracking system (Noldus-Ethovision). The total traveling distance and the movement time of each animal were recorded during the testing period using the EthoVision tracking system. The testing arena was thoroughly cleaned with 70% ethanol between each testing period for each mouse.

As shown in FIG. 1, there is a significant increase in the total tracking of the mice after PS128 treatment in the DDC gene conditional knockout mutant mice (DDC-ko) compared to that before the PS128 treatment. After treatment with PS128, the DDC gene conditional knockout mutant mice (DDC-ko) showed more motor activity compared to that before treatment.

Figure 2A:
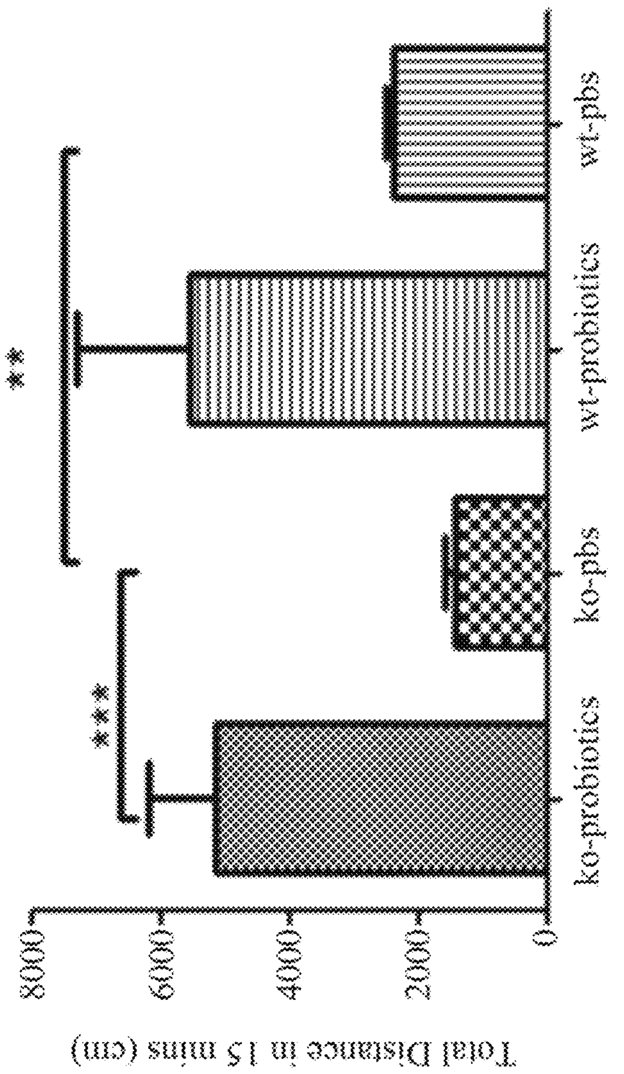
FIG. 2A and FIG. 2B show the results of basal locomotor activity including total distance in 15 minutes (FIG. 2A) and locomotion (FIG. 2B) in mice. ko-probiotics: mutant mice with the DDC gene knockout treated with PS128, n=21; ko-pbs: mutant mice with the DDC gene knockout treated with phosphate buffered saline, n=11; wt-probiotics: wildtype mice treated with PS128, n=11; wt-pbs: wildtype mice treated with phosphate buffered saline, n=12. $^{}p<0.005$, $^{*}p<0.0005$.
Figure 2B:
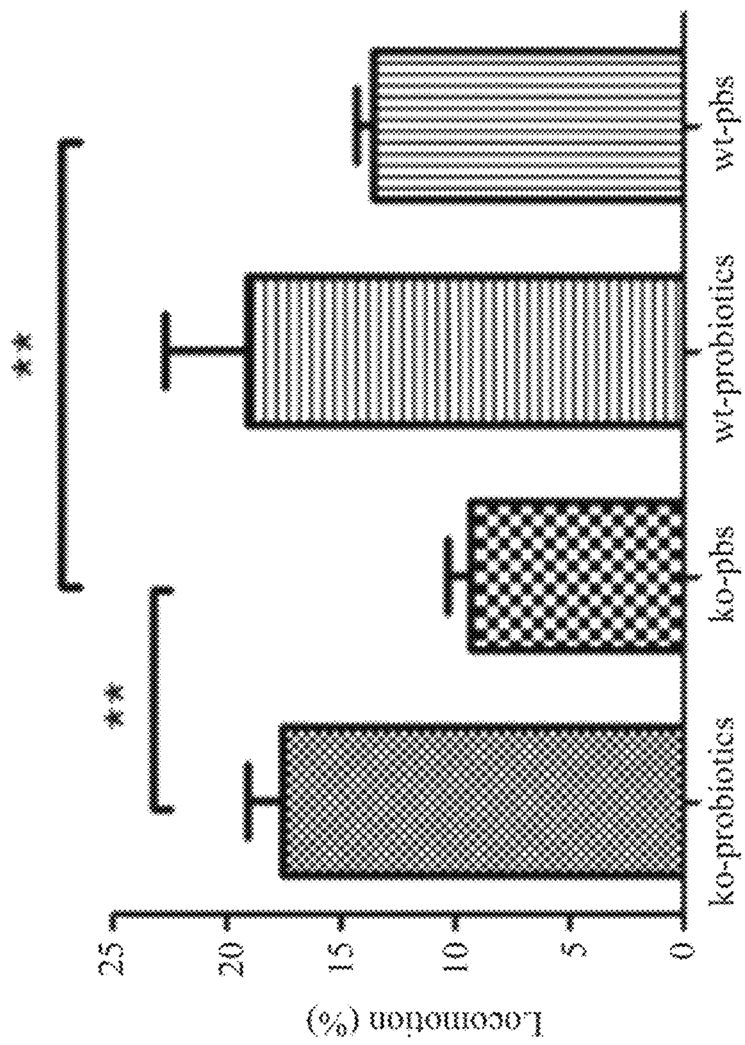

FIGS. 2A and 2B show the assessment result of basal locomotor activity in a specific activity arena for 15 minutes. The results showed that total moving distance (FIG. 2A) and the locomotion (FIG. 2B) of DDC-ko mice were worse than wildtype mice before treatment ($P<0.005$). However, after treatment with PS128, the condition was significantly improved in both total distance ($p<0.0005$) and locomotion ($P<0.005$). The numbers of mice in each group used in this assessment are n=21 for the DDC gene conditional knockout mutant mice treated with PS128 (ko-probiotics), n=11 for the wildtype mice treated with PS128 (wt-probiotics), n=11 for the DDC gene conditional knockout mutant mice treated with PBS (ko-pbs), and n=12 for the wildtype mice treated with pbs (wt-pbs).

Furthermore, rotarod performance test is carried out to serve as performance test based on a rotating rod with forced motor activity being applied. The test measures parameters such as riding time (seconds) or endurance. In the test, the mice were placed on a horizontally oriented, rotating cylinder (rod) suspended above a cage floor, which is low enough not to injure the animal, but high enough to induce avoidance of fall. Mice naturally try to stay on the rotating cylinder, or rotarod, and avoid falling to the ground. The length of time that a given animal stays on this rotating rod is a measure of their balance, coordination, physical condition, and motor-planning.

Figure 3:
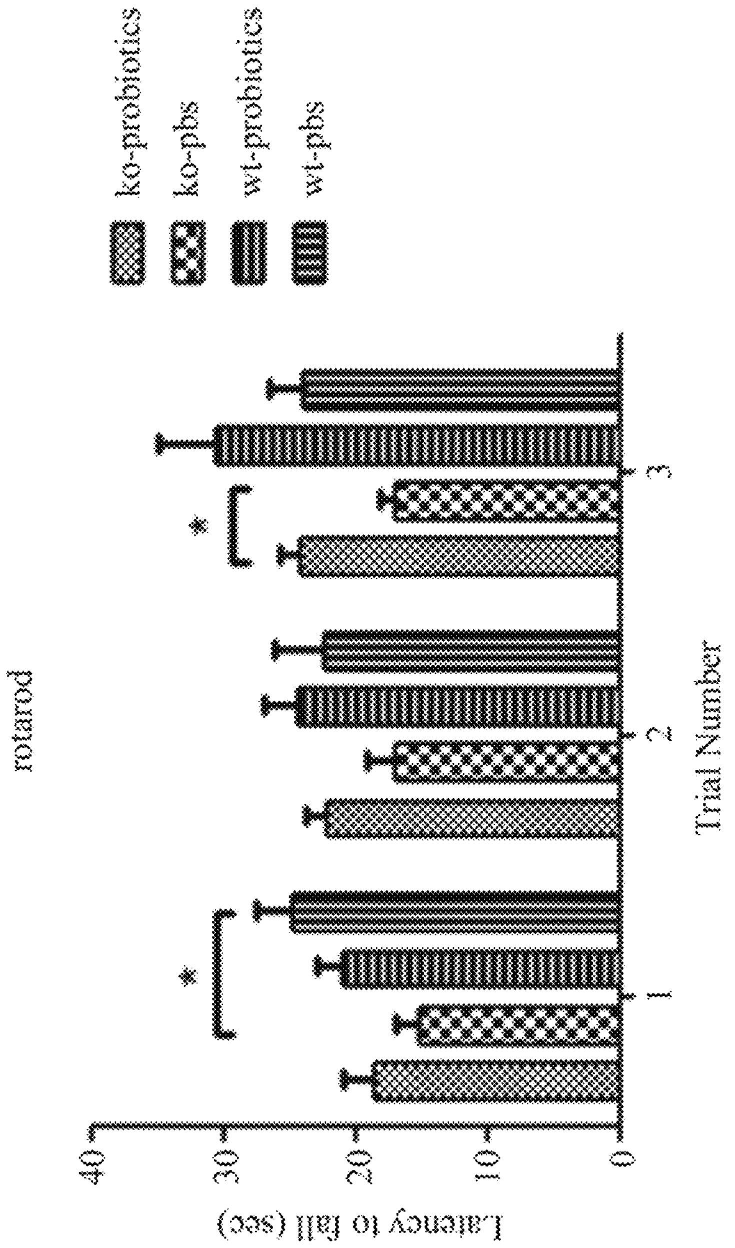
FIG. 3 shows the results of rotarod test in different mice. ko-probiotics: mutant mice with the DDC gene knockout treated with PS128; ko-pbs: mutant mice with the DDC gene knockout treated with phosphate buffered saline; wt-probiotics: wildtype mice treated with PS128; wt-pbs: wildtype mice treated with phosphate buffered saline.

Results of the rotarod test showed that before treatment, DDC-ko mice showed poor rotarod performance that was significantly worse than that of the wildtype mice. However, after PS128 treatment, although DDC-ko mice still showed poorer rotarod performance than the wildtype mice, the DDC-ko mice had significant improvement in the latency to fall on the rotarod test, when compared to the test before treatment ($P<0.05$), as shown by FIG. 3.

Example 2. Administration of PS128 Improves Neuron Branching

Figure 4A:
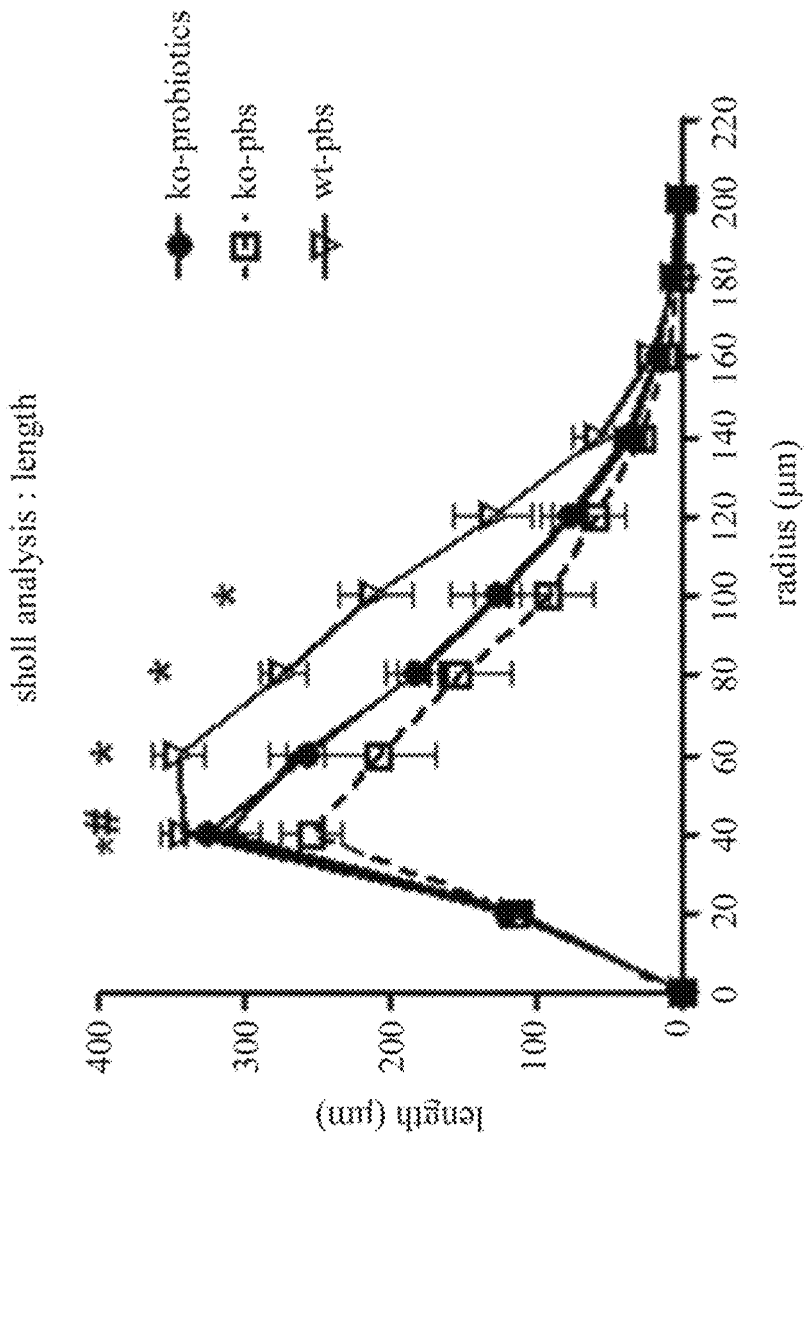
FIG. 4A and FIG. 4B show the effects of PS128 administration on neuron branching.
Figure 4B:
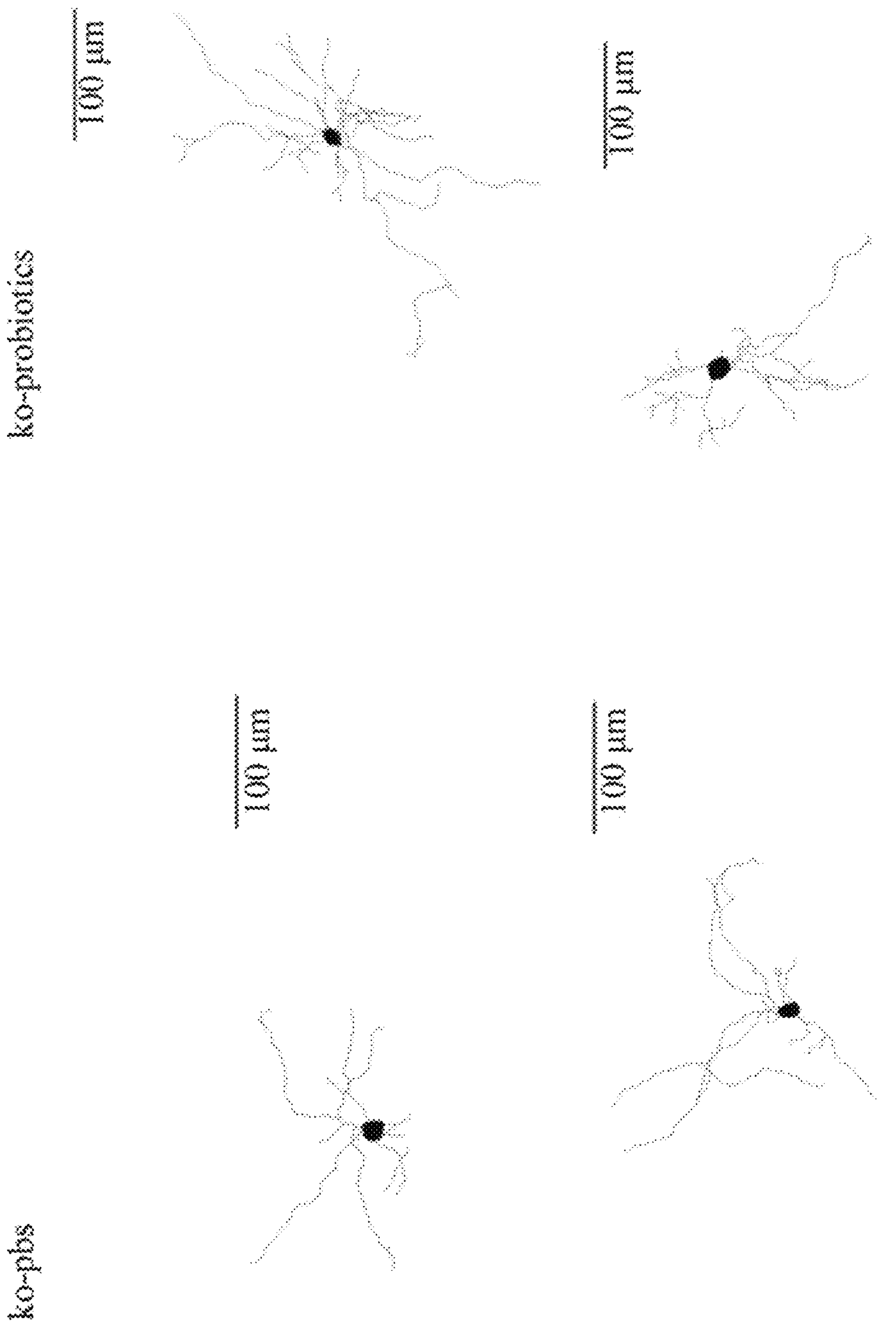

Golgi staining was used to evaluate the neuron branching condition before and after PS128 treatment. Golgi staining was done on the mouse brain after it has been removed and fixed. As shown in FIG. 4B, treatment with PS128 in the DDC-ko mice showed more neuronal branching compared to those treated with PBS.

For examining the length of neuron processes, the centrifugal method is used as the basic scheme to assign the branch order to a tree. The segment that begins at the origin of the dendrite is assigned the branch order 1. The branches that connect to that segment are assigned the branch order 2. The branches that connect to those branches are assigned the branch order 3. This process continues until all branches are assigned a value. Centrifugal ordering counts the distance from the root in terms of the number of segments traversed. The advantage to centrifugal ordering is that missing portions of the tree do not result in incorrect numbering of the known segments. The Sholl analysis is carried out to obtain the quantity of objects or the total length within shells. The Sholl analysis can be performed on the trees or markers on the trees. As shown in FIG. 4A, the results of Sholl analysis showed that the total length of all processes passing through a shell was significantly decreased in DDC-ko mice ($P<0.05$). However, after treatment with PS128, the total length significantly improved in DDC-ko mice ($P<0.05$). Therefore, treatment of PS128 improves neuron branching and improves neuron function and connectivity.

Example 3. Administration of PS128 Causes Alteration of Neurotransmitter Levels To examine the alteration of neurotransmitter levels by the administration of PS128, high-performance liquid chromatography with electrochemical detection was used to measure neurotransmitters in the brains of mice in different groups. The numbers of mice used in each group were shown in Tables 1 and 2 below.

Specific brain regions including the striatum and cortex were collected for the evaluation of neurotransmitter including dopamine (DA), dihydroxyphenylacetic acid (DOPAC), homovanillic acid (HVA), serotonin (5-HT), 5-hydroxyindoleacetic acid (5-HIAA), L-3,4-dihydroxyphenylalanine (L-DOPA) and 3-O-methyldopa (3OMD).

As shown in Tables 1 and 2 below, after treatment with PS128, dopamine, serotonin, and their metabolites were increased while L-DOPA was decreased in cerebral cortex (Table 1).

In addition, in striatum, the dopamine, serotonin, and 5-HIAA were significantly increased ($P<0.05$), and L-DOPA was significantly decreased after treatment with PS128 (Table 2). These results indicated that PS128 increased the dopaminergic and serotoninergic functions in DDC-ko mice.

TABLE 1

The neurotransmitters and their metabolites in cerebral cortex

| Neurotransmitter(ng/mg protein) from cortex | | dopac | da | 5hiaa | hva | 5ht | ldopa | 3OMD |
|---|---|---|---|---|---|---|---|---|
| 1. DDC-ko-pbs(n = 10) | | 51 ± 13.8 | 50.5 ± 45 | 22.6 ± 9.2 | 30 ± 12.7 | 21.5 ± 6.8 | 29.9 ± 16.1 | 36.3 ± 23.6 |
| 2. DDC-ko-Probioticin = 10) | | 95.2 ± 42.5 | 118 ± 78.9 | 41.1 ± 25.7 | 47.3 ± 15.4 | 36.1 ± 24.2 | 18.8 ± 16.3 | 29.7 ± 15.4 |
| 3. wt-pbs(n = 5) | | 149 ± 57.4 | 178.4 ± 84.8 | 122 ± 64.3 | 71.2 ± 27.5 | 86.6 ± 18.7 | 2.2 ± 1.9 | 44 ± 18 |
| 4. wt-probiotic(n = 5) | | 133.6 ± 49.1 | 180.1 ± 157.1 | 82.5 ± 12.6 | 66.3 ± 25.1 | 64.7 ± 28.4 | 3.5 ± 2.8 | 41.7 ± 24.5 |
| Post-hoc (bonferroni) | p < 0.05 | 1vs3,4 | 1vs3 | 1vs3,4; 2vs3 | 1vs3,4; 3vs all | 1vs3,4; 2vs3,4 | 1vs3,4 | |

DDC-ko-pbs: mutant mice with the DDC gene knockout treated with phosphate buffered saline
DDC-ko-probiotics: mutant mice with the DDC gene knockout treated with PS128
wt-pbs: wildtype mice treated with phosphate buffered saline
wt-probiotics: wildtype mice treated with PS128

TABLE 2

The neurotransmitters and their metabolites in striatum

| Neurotransmitter (ng/mg protein) from Striatum | | dopac | da | 5hiaa | hva | 5ht | ldopa | 3OMD |
|---|---|---|---|---|---|---|---|---|
| 1. DDC-ko-pbs(n = 11) | | 476 ± 268.9 | 570 ± 231 | 35.5 ± 6.6 | 180.5 ± 63.8 | 24.4 ± 10.3 | 73 ± 34.1 | 131.1 ± 53.2 |
| 2. DDC-ko-Probiotic(n = 11) | | 647.8 ± 430.8 | 823.6 ± 163.9 | 72.9 ± 34.8 | 184.9 ± 84 | 47.1 ± 14.8 | 18.1 ± 24.9 | 139.8 ± 23.2 |
| 3. wt-pbs(n = 10) | | 657.5 ± 341.2 | 836.2 ± 231.2 | 97.1 ± 34.4 | 190.6 ± 77.7 | 60.2 ± 17 | 5.6 ± 6.2 | 176.5 ± 45.1 |
| 4. wt-probiotic(n = 12) | | 633.6 ± 417.2 | 703.5 ± 146.8 | 103.9 ± 30.9 | 215.5 ± 93.7 | 58.6 ± 10 | 9.3 ± 8.6 | 146.1 ± 28.7 |
| Post-hoc (bonferroni) | p < 0.05 | | 1vs2,3 | 1vs all | | 1 vs all | 1 vs all | |

DDC-ko-pbs: mutant mice with the DDC gene knockout treated with phosphate buffered saline
DDC-ko-probiotics: mutant mice with the DDC gene knockout treated with PS128
wt-pbs: wildtype mice treated with phosphate buffered saline
wt-probiotics: wildtype mice treated with PS128

Example 4. Improvement of AADC Symptoms in Subjects Supplemented with PS128

An open-label, single-dose study was conducted to examine the efficacy of probiotics PS128 in pediatric subjects with AADC deficiency. The probiotic capsules weighed 425±25 mg and contained $3\times10^{10}$ CFU/capsule of PS128, with microcrystalline cellulose as the carrier. All capsules were identical in taste and appearance and provided by Bened Biomedical Co., Ltd. They were stored at a refrigerated temperature of 4° C. to 8° C. Oral administrations of 1 capsule of PS128 were given on a 12-hour time interval daily to participants in the treatment of AADC deficiency and treated for 14 months. Evaluation was done before and after PS128 treatment.

A total of 11 patients completed treatment for 14 months. After evaluation, the most significant difference in clinical presentations is decrease in sweating (P<0.01). There was also decrease in irritability after treatment. Dystonia was mildly improved in 10 patients, that is, in 91% of the patients receiving the PS128 treatment. Disturbance of sleep was improved in 3 patients, which is in 27% of the patients receiving the PS128 treatment.

While some of the embodiments of the present disclosure have been described above, it is, however, possible for those of ordinary skill in the art to make various modifications and changes to these embodiments shown without substantially departing from the teaching of the present disclosure. Such modifications and changes are encompassed in the scope of the present disclosure as set forth in the appended claims.

The invention claimed is:

1. A method for treating aromatic L-amino acid decarboxylase (AADC) deficiency in a subject in need thereof, comprising administering a composition comprising an effective amount of *Lactobacillus plantarum* subsp. *plantarum* PS128 and a carrier thereof to the subject, wherein the administration of the composition improves at least one symptom of L-amino acid decarboxylase (AADC) deficiency in the subject, and wherein the symptom is a neurological symptom.

2. The method of claim 1, wherein the administration alters a level of a neurotransmitter in the subject.

3. The method of claim 2, wherein the neurotransmitter is selected from the group consisting of dihydroxyphenylacetic acid (DOPAC), homovanillic acid (HVA), serotonin (5-HT), 5-hydroxyindoleacetic acid (5-HIAA), L-3,4-dihydroxyphenylalanine (L-DOPA) and 3-O-methyldopa (3OMD).

4. The method of claim 2, wherein the administration increases dopaminergic and serotoninergic functions in the subject.

5. The method of claim 1, wherein the administration improves neuron branching in the subject.

6. The method of claim 5, wherein the administration improves neuron function and connectivity.

7. The method of claim 1, wherein the symptom includes sweating, dystonia, irritability and sleep disturbance.

8. The method of claim 1, wherein the neurological symptom comprises motor activity, basal locomotor activity, balance, coordination, physical condition, motor planning, and any combination thereof.

9. The method of claim 1, wherein the composition is orally administered to the subject.

10. The method of claim 1, wherein the composition is a pharmaceutical composition, and the carrier is a pharmaceutically acceptable carrier thereof.

11. The method of claim 1, wherein the composition contains at least $1\times10^9$ CFU of the *Lactobacillus plantarum* subsp. *plantarum* PS128.

12. The method of claim 1, wherein the composition is administered to the subject at least once a day.

13. The method of claim 1, wherein the composition is administered to the subject for at least one week.

* * * * *